United States Patent [19]

Mersch

[11] Patent Number: 5,468,238
[45] Date of Patent: Nov. 21, 1995

[54] ENDOSCOPIC LASER INSTRUMENT

[75] Inventor: Steven H. Mersch, Germantown, Ohio

[73] Assignee: Ethicon, Inc., Somerville, N.J.

[21] Appl. No.: 74,626

[22] Filed: Jun. 11, 1993

[51] Int. Cl.$^6$ ................................................ A61B 17/36
[52] U.S. Cl. .................... 606/15; 606/2; 606/17; 600/108
[58] Field of Search ...................... 128/4; 606/15, 606/16, 14, 2, 3, 10, 11, 12, 17

[56] References Cited

U.S. PATENT DOCUMENTS

| | | | |
|---|---|---|---|
| 3,720,213 | 3/1973 | Hobart et al. | 606/15 |
| 3,865,113 | 2/1975 | Sharon et al. | 606/15 |
| 4,266,548 | 5/1981 | Davi | 606/15 |
| 4,852,567 | 8/1989 | Sinofsky | 606/3 |
| 5,121,740 | 6/1992 | Uram | 128/6 |
| 5,125,922 | 6/1992 | Dwyer et al. | 606/10 |

FOREIGN PATENT DOCUMENTS

| | | | |
|---|---|---|---|
| 3730563 | 3/1989 | Germany | 606/10 |
| 9012679 | 8/1992 | WIPO | 606/15 |

OTHER PUBLICATIONS

Schuman et al "Energy Levels and Probe Placement in Contact Transscleral Semiconductor Diode Laser Cyclophotocoagulation in Human Cadaver Eyes" Nov. 1991 pp. 1534–1537.

*Primary Examiner*—Michael H. Thaler
*Assistant Examiner*—Sonya Harris-Ogugua

[57] ABSTRACT

An endoscopic instrument having a diode laser at the distal end of the instrument for cutting and/or coagulating tissue during an endoscopic procedure.

8 Claims, 3 Drawing Sheets

ENDOSCOPIC LASER INSTRUMENT

FIELD OF THE INVENTION

This invention relates to an instrument for use in video assisted, minimally invasive surgery. For example, endoscopy, laparoscopy, or other optically assisted viewing procedures. More specifically, the invention relates to an instrument for cutting and/or coagulating tissue in an endoscopic procedure. The term "endoscopic" as used herein is meant to refer to any surgical procedure using either natural body openings and/or small artificial openings made by puncture or incision.

BACKGROUND OF THE INVENTION

Endoscopic surgery has gained wide acceptance as an improved and cost effective technique for conducting certain surgical procedures. In endoscopic surgery, a trocar, which is a pointed piercing device, is inserted into the body with a cannula placed around the trocar. After the trocar pierces the abdominal wall, it is removed and the cannula remains in the body. Through this cannula, endoscopic procedures are possible. Often, multiple openings are produced in the body with a trocar so that an endoscopic instrument may be placed in one cannula, appropriate viewing and illuminating means placed in another cannula and so forth. As more is learned about endoscopic surgical procedures and more instruments developed, the type of procedures that may be performed will increase. Presently, some procedures include gall bladder, diagnostic procedures, bowel resections, joint repair, tissue repair and various sterilization procedures.

In many of these endoscopic procedures, it is necessary to cut tissue or coagulate tissue or sometimes both. A number of devices have been developed for cutting tissue such as knives and lasers and a number of devices have been developed for coagulating tissue, again using lasers or cauterizing devices. When lasers have been used to either cut or coagulate tissue, the laser is outside the body and a laser beam is delivered within the body cavity through appropriate fiber optics. By delivering the laser beam through a fiber optic, considerable energy is required to obtain the necessary power at the distal tip of the fiber optic. This type of delivery also causes the laser beam to lose spatial coherence and, hence, makes it impossible to efficiently focus the light to a diffraction limited spot.

It is an object of the present invention to provide a laser beam within the body cavity that has excellent spatial coherence. It is a further object of the present invention to provide a laser beam at the distal tip of an endoscopic instrument from relatively low energy lasers. It is yet another object of the present invention to provide a laser beam that may be used to both coagulate and cut tissue in an endoscopic procedure.

SUMMARY OF THE PRESENT INVENTION

The present invention provides an endoscopic instrument for cutting and/or coagulating tissue in endoscopic surgery. Broadly, the instrument has a distal end which is positioned within the body cavity and a proximal end which is positioned outside of the body cavity and is manipulated by the user to operate the distal end. The distal and proximal ends are connected by an elongated tubular shaft as is well known in the art. A diode laser is disposed in the distal end of the instrument. Means are disposed in the instrument for maintaining said laser at a desired temperature during use, i.e., for keeping the laser sufficiently cool so that it will not harm surrounding tissue and so it has an acceptable operating cycle time. In certain embodiments of the present invention where the laser is able to emit one or more wavelengths, means are disposed extending from the distal end of the instrument to show the location of the focus point of the wavelength or lengths as desired.

DETAILED DESCRIPTION OF THE DRAWINGS

Figure 1:
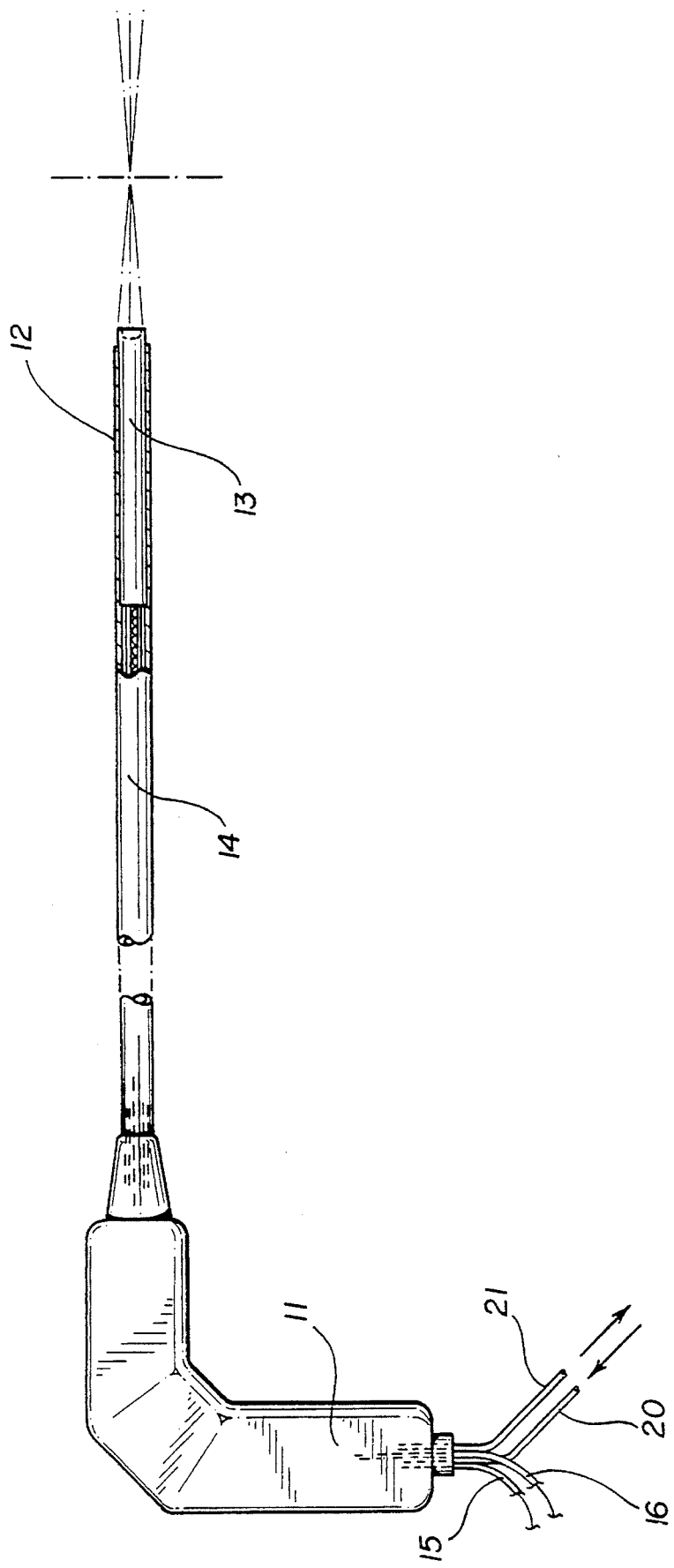
FIG. 1 is a side elevational view of one embodiment of an endoscopic laser instrument of the present invention.

Referring to the drawings, in FIG. 1 there is shown a side elevational view of the simplest form of an endoscopic laser instrument according to the present invention. The instrument 10 comprises a handle 11 disposed at the proximal end of the instrument. The distal end 12 of the instrument has a diode laser 13. The diode laser is enclosed in a suitable shaft 14 which extends from the laser to the handle of the instrument. A power supply, 17, is connected by a cable 15 extending through the handle and the shaft to the laser to supply power to the laser. A second cable 16 to monitor the output of the instrument also extends through the handle through the shaft to the laser. If desired, the power supplied to the laser may be controlled by either a switch on the handle of the instrument or by an external switch, either hand operated or foot operated. In the embodiment shown, the laser is cooled by circulating water. The instrument includes an inlet 20 which extends through the handle to the space between the laser and the shaft enclosing the laser. An outlet tube 21 also extends from the shaft enclosing the laser back through the shaft and out through the handle. Suitable supply means, not shown for the sake of clarity, supplies cool water about the laser to maintain the desired temperature whereby a laser beam having a spacial coherence and temporal coherence is maintained during the use of the instrument.

The lasers used in the instruments of the present invention are the solid state, semi-conductor laser diodes. These lasers may be powered by a 9-volt battery or by other similar power sources. The wavelength of the laser may vary but lasers are currently available in the range of from about 1300 nm to 1550 nm for cutting tissue and in the range of from about 670 nm to 1300 nm for coagulating material. The power required for cutting or coagulating is at least 3 watts. A very low powered laser, down to the 10 miliwatt range, may be used for diagnostic purposes or for initiating other operations and the like. Examples of suitable lasers for cutting tissue or coagulating material are those identified as InGaAs and InGaAsP and sold by Spectra Diode Labs and McDonnel Douglas.

Figure 2:
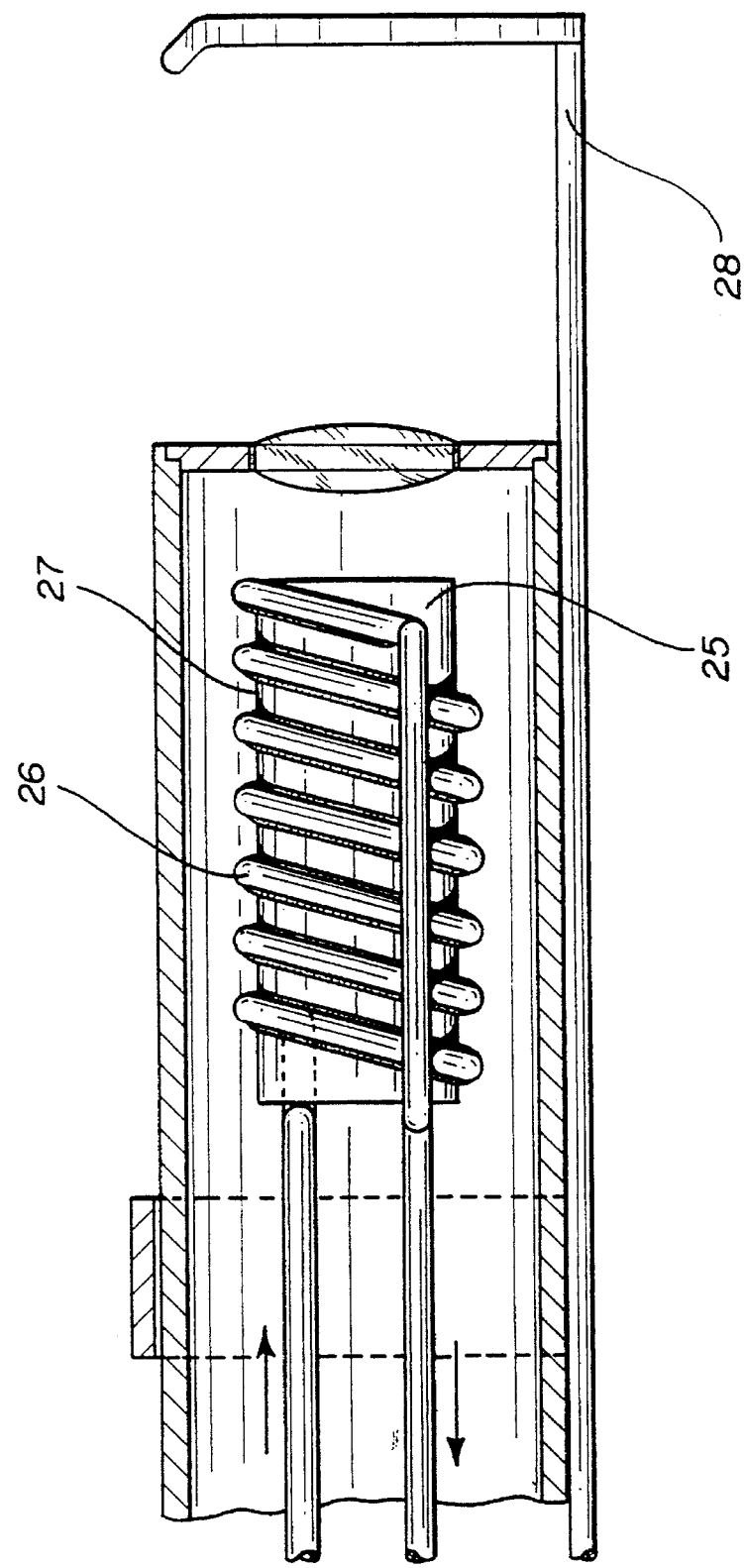
FIG. 2 is an enlarged side elevational view showing one means for cooling the laser in an instrument of the present invention.

Referring to FIG. 2 of the drawings, there is shown an enlarged cross-sectional view of the distal end of an instrument of the present invention. The distal end carries a diode laser 25 as previously described. The distal end of the instrument also carries an extension guide 28 to indicate the focus point of the laser beam. Surrounding the diode laser is a cooling mechanism. The cooling mechanism comprises helically wound copper tubing 26 soldered to the outside casing 27 of the laser. This chamber is cooled by circulating water in the direction shown by the arrows through the tubing. As previously mentioned, in certain instances, depending on the use to be made of the laser, it may not be necessary to provide separate cooling means for the diode laser. The shaft of the instrument or an air space between the laser and the shaft may be a sufficient heat sink to provide the desired cooling of the laser. The higher the power of the laser the greater the possibility that the laser will have to be cooled during use. Often, passive cooling may be accomplished if the laser is pulsed and active cooling may be required if the laser beam is continuous.

Figure 3:
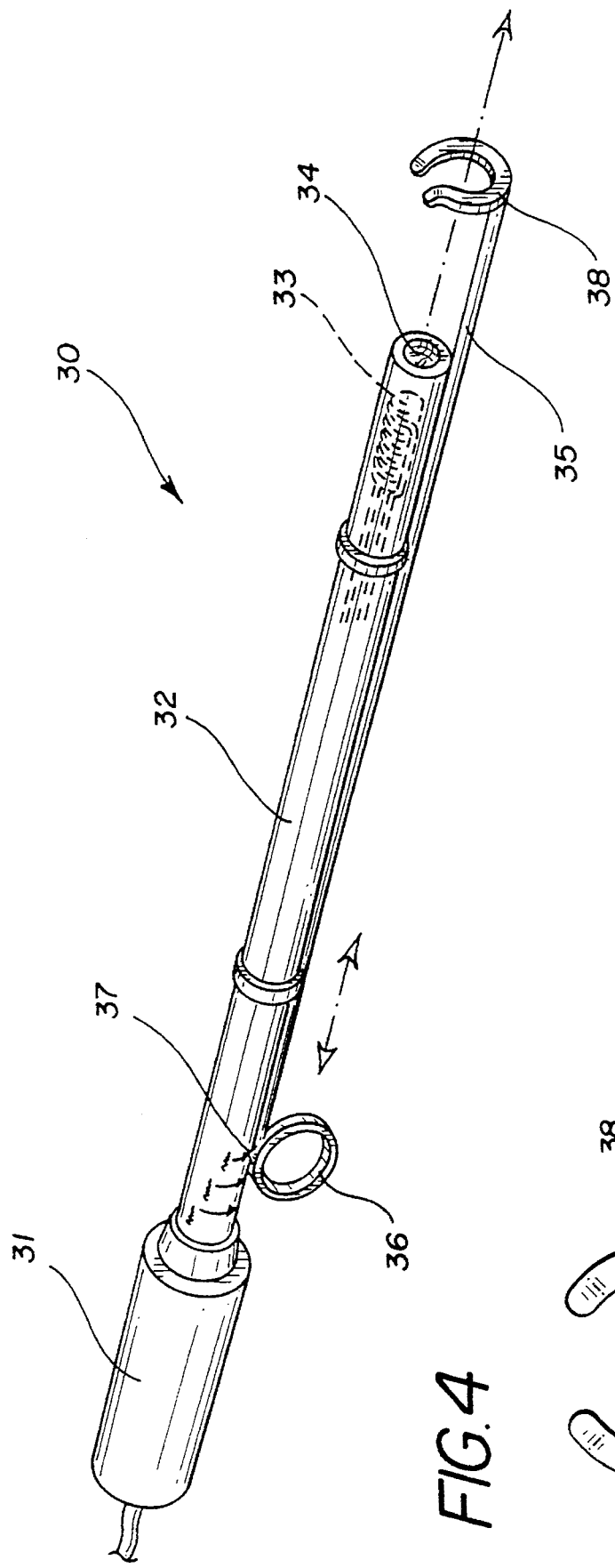
FIG. 3 is a perspective view of an endoscopic laser instrument showing an extension mechanism used on the end of the instrument to show the focus point.
Figure 4:
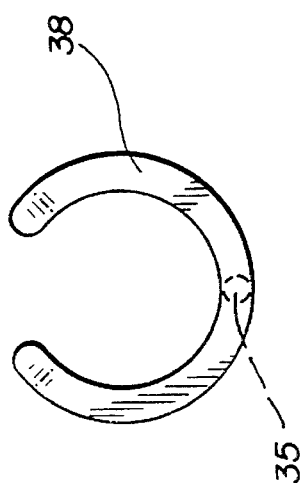
FIG. 4 is an end view of the extension guide depicted in FIG. 3.

Referring to FIGS. 3 and 4, there is shown another embodiment of a surgical laser instrument according to the present invention. In this embodiment, the instrument 30 comprises a proximal handle portion 31. Extending from the handle is an elongate shaft 32. Disposed in the distal portion of the shaft is a diode laser 33. At the distal end of the shaft is a suitable focusing lens 34. The lens 34 and the diode laser 33 are arranged to provide a spatially coherent beam. Extending along the shaft from the handle portion to beyond the distal end of the shaft is an extension guide 35. The extension guide is slidably mounted on the shaft so that it may be moved longitudinally of the shaft. The proximal end of the extension guide has a finger loop 36. Indicating means 37 is disposed on the outside of the shaft. The distal end of the extension guide terminates in a semi-circular loop 38. By sliding the extension guide along the shaft, the semicircular guide may be placed at the focal point of the laser beam to provide coagulation, welding or cutting as desired.

Having now described certain specific embodiments of the present invention, it will be readily apparent to those skilled in the art that various modifications and variations may be made to the present invention without departing from the spirit and scope thereof.

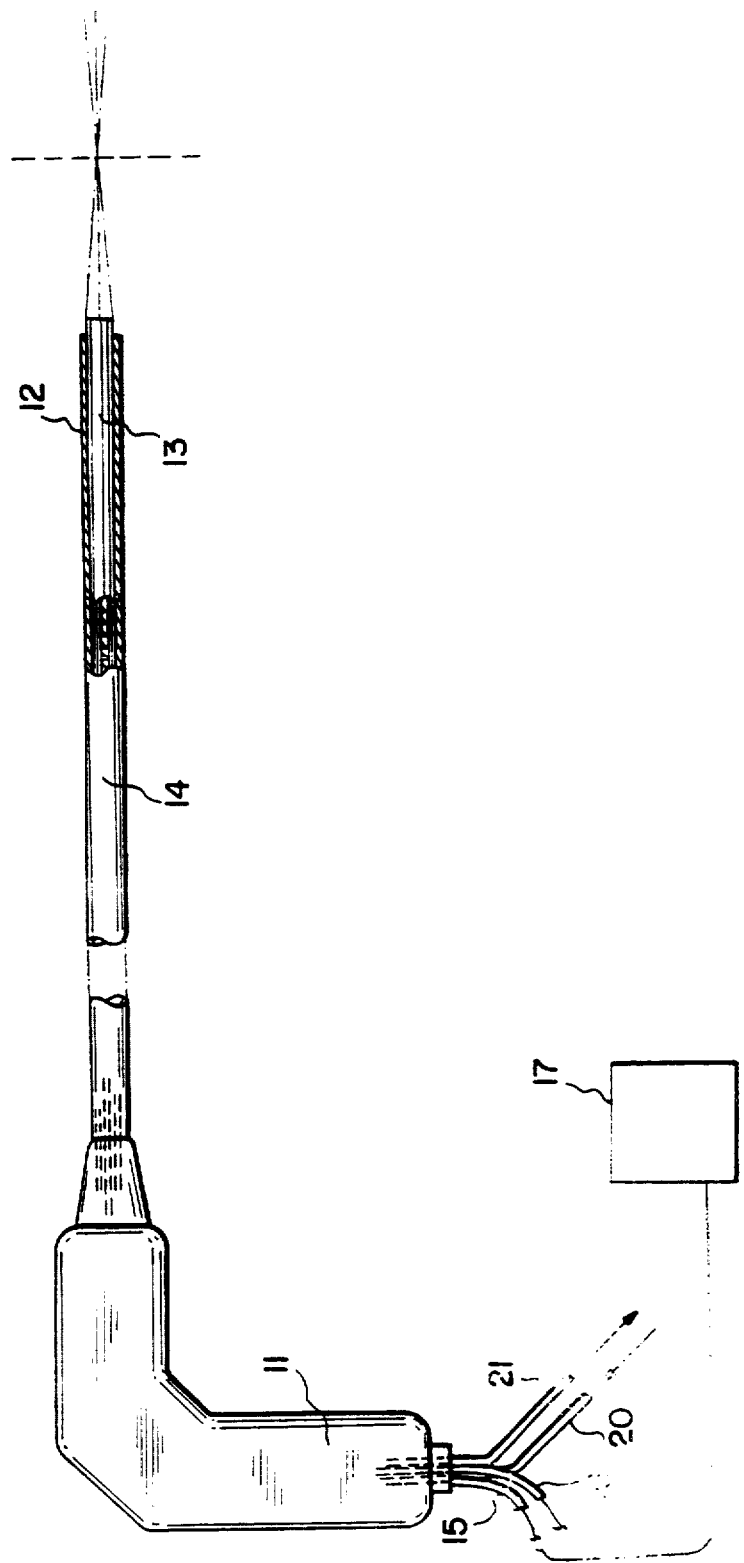

What is claimed is:

1. An endoscopic instrument that provides a spatially coherent beam for use in an endoscopic procedure, said instrument having a distal end to be positioned within a body cavity of a mammal, a proximal end for manipulating said instrument from outside a body of a mammal and an elongated shaft portion connecting said distal and proximal ends, a diode laser and a focussing means for providing said spatial coherent beam, disposed in the distal end of said shaft portion and means for supplying power to said laser at the distal end of the instrument.

2. An endoscopic instrument according to claim 1 including means disposed in the distal end of the instrument for cooling said laser during use.

3. An endoscopic instrument according to claim 1 wherein the diode laser provides a laser beam for cutting tissue, said beam having a wavelength of from about 1300 nm to 1550 nm.

4. An endoscopic instrument according to claim 1 wherein the diode laser provides a laser beam for coagulating material, said beam having a wavelength of from about 670 nm to 1300 nm.

5. An endoscopic instrument according to claim 1 including means extending from the distal end of the instrument for indicating a focal point of a laser beam.

6. An endoscopic instrument according to claim 1 wherein the diode laser is low power and useful for diagnostic purposes.

7. An endoscopic instrument for cutting tissue and coagulating material during an endoscopic procedure, said instrument having a distal end to be positioned within a body cavity of a mammal, a proximal end for manipulating said instrument from outside a body of a mammal, an elongate shaft portion connecting said distal and proximal ends, a diode laser and a focussing lens disposed in the distal end of said shaft portion, means for supplying power to said laser at the distal end of the instrument, means disposed in said shaft portion for cooling said laser during use of the instrument; focussing means for providing said laser beam with spatial coherence and temporal coherence.

8. An endoscopic instrument according to claim 7 wherein the diode laser produces a first laser beam having a wavelength of from 670 nm to 1300 nm to be used for coagulating material and a second laser beam having a wavelength of from 1300 nm to 1550 nm to be used for cutting tissue.

\* \* \* \* \*

UNITED STATES PATENT AND TRADEMARK OFFICE
CERTIFICATE OF CORRECTION

PATENT NO. : 5,468,238

DATED : November 21, 1995

INVENTOR(S) : Steven H. Mersch

It is certified that error appears in the above-indentified patent and that said Letters Patent is hereby corrected as shown below:

In the Drawings:

Reference numeral 17 was omitted from Figure 1. See new copy of Figure 1 attached herewith.

Signed and Sealed this

Fourth Day of June, 1996

*Attest:*

BRUCE LEHMAN

*Attesting Officer*     *Commissioner of Patents and Trademarks*